(12) United States Patent
Konkle et al.

(10) Patent No.: US 8,062,040 B2
(45) Date of Patent: Nov. 22, 2011

(54) APPARATUS AND METHOD FOR ELECTRICAL CONNECTION CLAMPING

(75) Inventors: Nicholas Ryan Konkle, Waukesha, WI (US); Michael Richard Moritz, Brookfield, WI (US); Thomas Michael Corcoran, Winona, MN (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/433,474

(22) Filed: Apr. 30, 2009

(65) Prior Publication Data

US 2011/0059660 A1    Mar. 10, 2011

(51) Int. Cl.
*H01R 12/00* (2006.01)
(52) U.S. Cl. ............................................. 439/74
(58) Field of Classification Search ............... 439/67, 439/74
See application file for complete search history.

(56) References Cited

U.S. PATENT DOCUMENTS

| 3,841,289 | A |   | 10/1974 | Meyers |
| 4,438,543 | A |   | 3/1984 | Noguchi et al. |
| 4,808,112 | A | * | 2/1989 | Wood et al. ............... 439/66 |
| 6,017,244 | A | * | 1/2000 | Daane ................... 439/495 |
| 6,074,333 | A |   | 6/2000 | Rajala et al. |
| 7,553,166 | B2 | * | 6/2009 | Gobron ................... 439/67 |

* cited by examiner

*Primary Examiner* — Phuong Dinh
(74) *Attorney, Agent, or Firm* — The Small Patent Law Group; Dean D. Small

(57) ABSTRACT

An apparatus and method for electrical connection clamping are provided. The apparatus includes a connection arrangement having a top clamp section and a bottom clamp section. The connection arrangement further includes a stacked connector between the top clamp section and the bottom clamp section. The top clamp section and the bottom clamp section are configured to distribute a compression force along a plurality of points of the stacked connector.

19 Claims, 14 Drawing Sheets

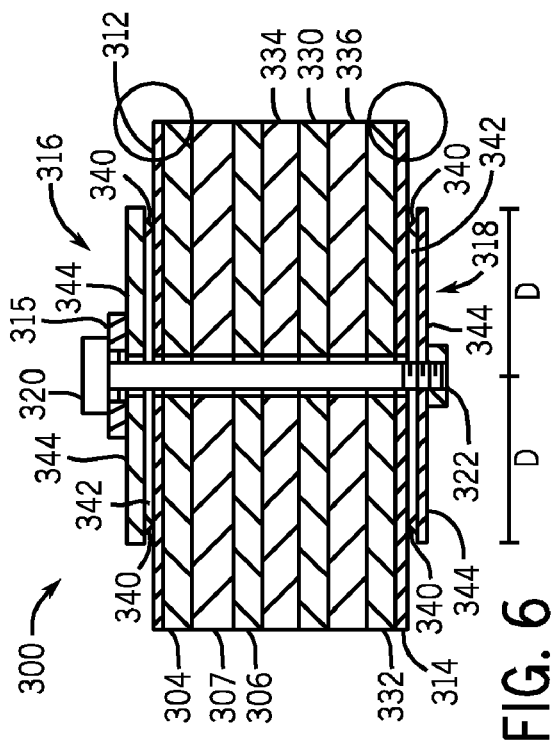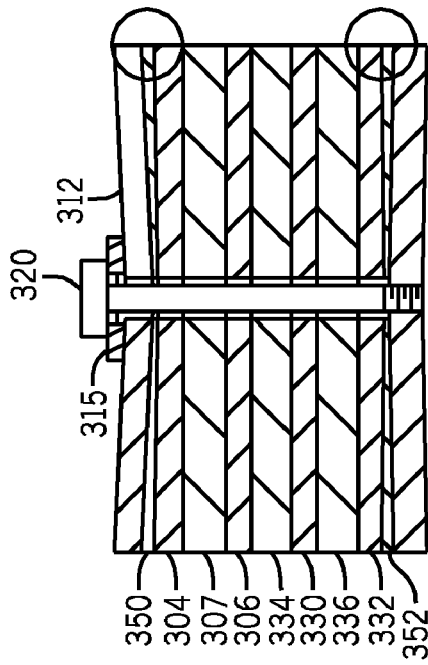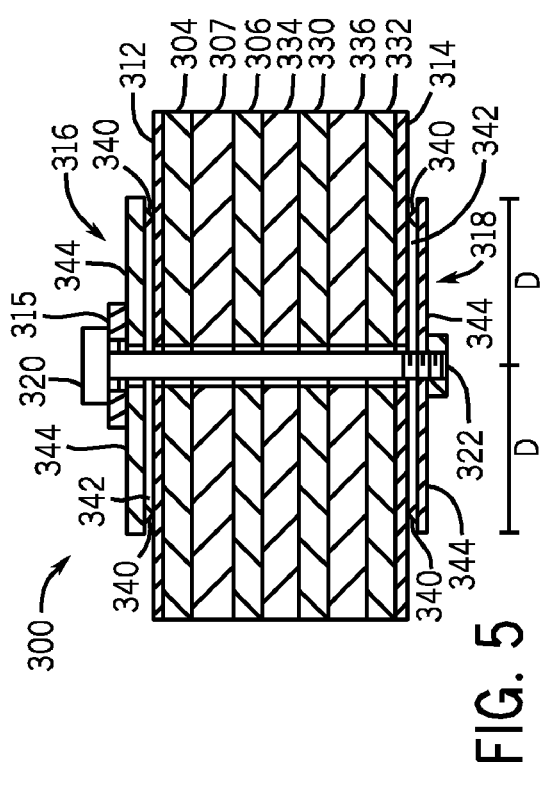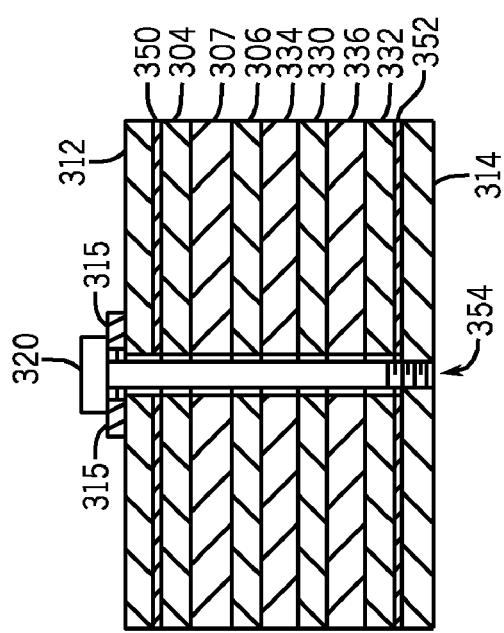
FIG. 5
FIG. 6
FIG. 7
FIG. 8

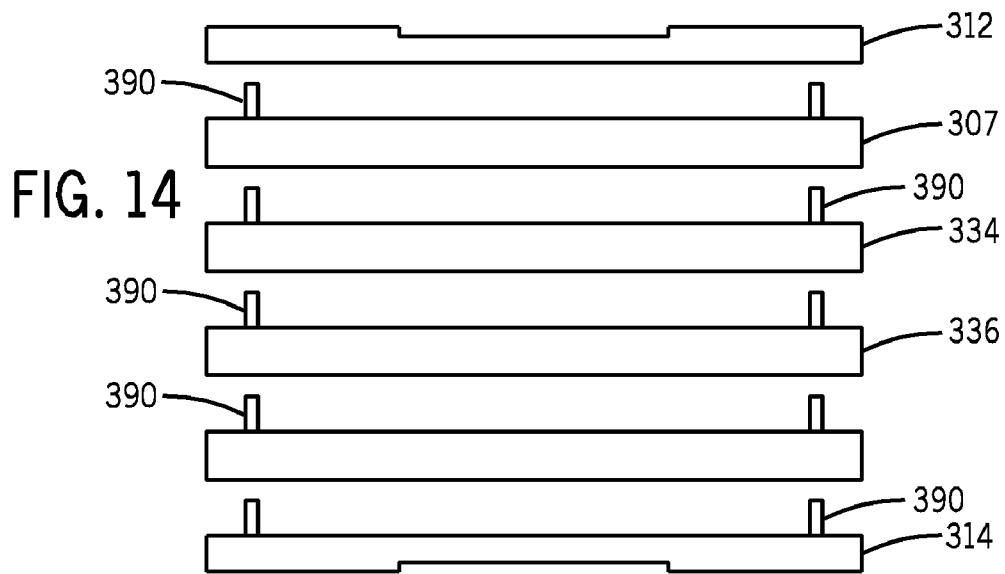
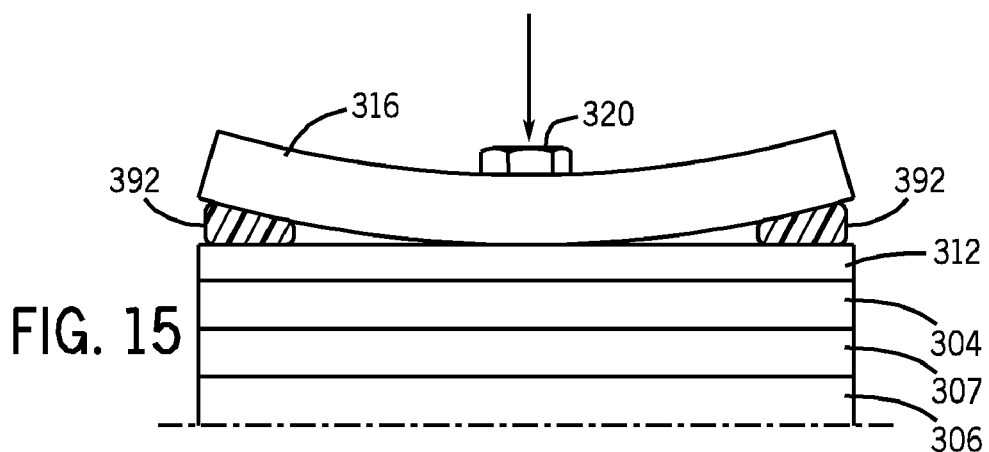
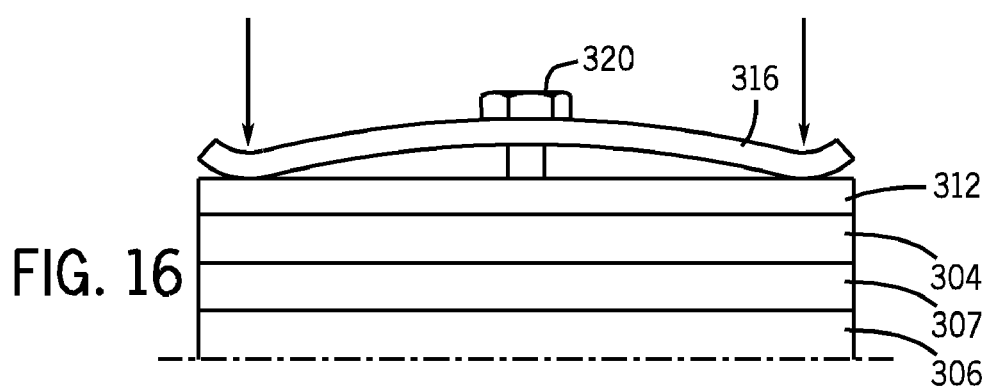

APPARATUS AND METHOD FOR ELECTRICAL CONNECTION CLAMPING

BACKGROUND OF THE INVENTION

The subject matter disclosed herein relates generally to electrical connectors, and more particularly to a connection and clamping arrangement for facilitating electrical connections, especially electrical connections between components in diagnostic imaging systems.

Electrical mating arrangements are used to maintain the connection between electrical components in systems. For example, different clamping arrangements are known to secure and maintain contact connections between ends of different electrical connectors.

In diagnostic imaging systems, high density electrical connections are often needed in order to communication high volumes of data between the components therein. For example, in ultrasound imaging systems, stacks of connectors (e.g., circuit boards or flexible circuits) are used to interconnect the transducer array in the scanhead of the ultrasound probe with an interface or other controller that connects to a system cable for controlling operation of the ultrasound probe.

High density electrical connections in these systems are created by clamping together the connectors, for example, a stack of circuit boards having exposed ends. In order to ensure proper electrical connection, adequate pressure is needed to align and maintain the connection of the connector ends. For example, in ultrasound imaging systems, a bolt is often used to apply a pressure to the electrical connector stack. However, the application of pressure using this bolt can result in the separation or lack of adequate pressure at the outer edges or exposed contacts of the electrical connector stack. Accordingly, proper electrical connection between the components within the system may not be made or maintained. Moreover, because of space constraints in some of these diagnostic imaging systems, for example, in an ultrasound imaging systems, the space available for securing the electrical connector stack is limited.

BRIEF DESCRIPTION OF THE INVENTION

In accordance with an embodiment of the invention, a connection arrangement for a stacked connector in a diagnostic imaging system is provided. The connection arrangement includes a top clamp section and a bottom clamp section. The connection arrangement further includes a stacked connector between the top clamp section and the bottom clamp section. The top clamp section and the bottom clamp section are configured to distribute a compression force along a plurality of points of the stacked connector.

In accordance with another embodiment of the invention, a connector for an ultrasound probe is provided. The connector includes a plurality of transducer flexible cables and a plurality of processing boards. The plurality of flexible cables and the plurality of processing boards form a stacked connector. The connector further includes a clamping arrangement configured to apply pressure to the stacked connector to electrically connect the plurality of transducer flexible cables and the plurality of processing boards. The clamping arrangement is configured to distribute a compression force from the applied pressure along a plurality of points of the stacked connector.

In accordance with yet another embodiment of the invention, a method for interconnecting components within a diagnostic imaging system is provided. The method includes aligning a plurality of flexible circuits to form a stacked connector and distributing a compression force along a plurality of points of the stacked connector.

BRIEF DESCRIPTION OF THE DRAWINGS

FIG. 5 is a cross-sectional view of a connection arrangement for a stacked connector formed in accordance with an embodiment of the invention.

FIG. 6 is a cross-sectional view of the connection arrangement of FIG. 6 illustrating a compression force.

FIG. 7 is a cross-sectional view of a connection arrangement for a stacked connector formed in accordance with another embodiment of the invention.

FIG. 8 is a cross-sectional view of the connection arrangement of FIG. 7 illustrating a compression force.

FIG. 14 is a side elevation view of top and bottom clamp sections and spacers formed in accordance with various embodiments of the invention.

FIG. 15 is a cross-sectional view of a connection arrangement for a stacked connector formed in accordance with another embodiment of the invention.

FIG. 16 is a cross-sectional view of a connection arrangement for a stacked connector formed in accordance with another embodiment of the invention.

DETAILED DESCRIPTION OF THE INVENTION

Figure 1:
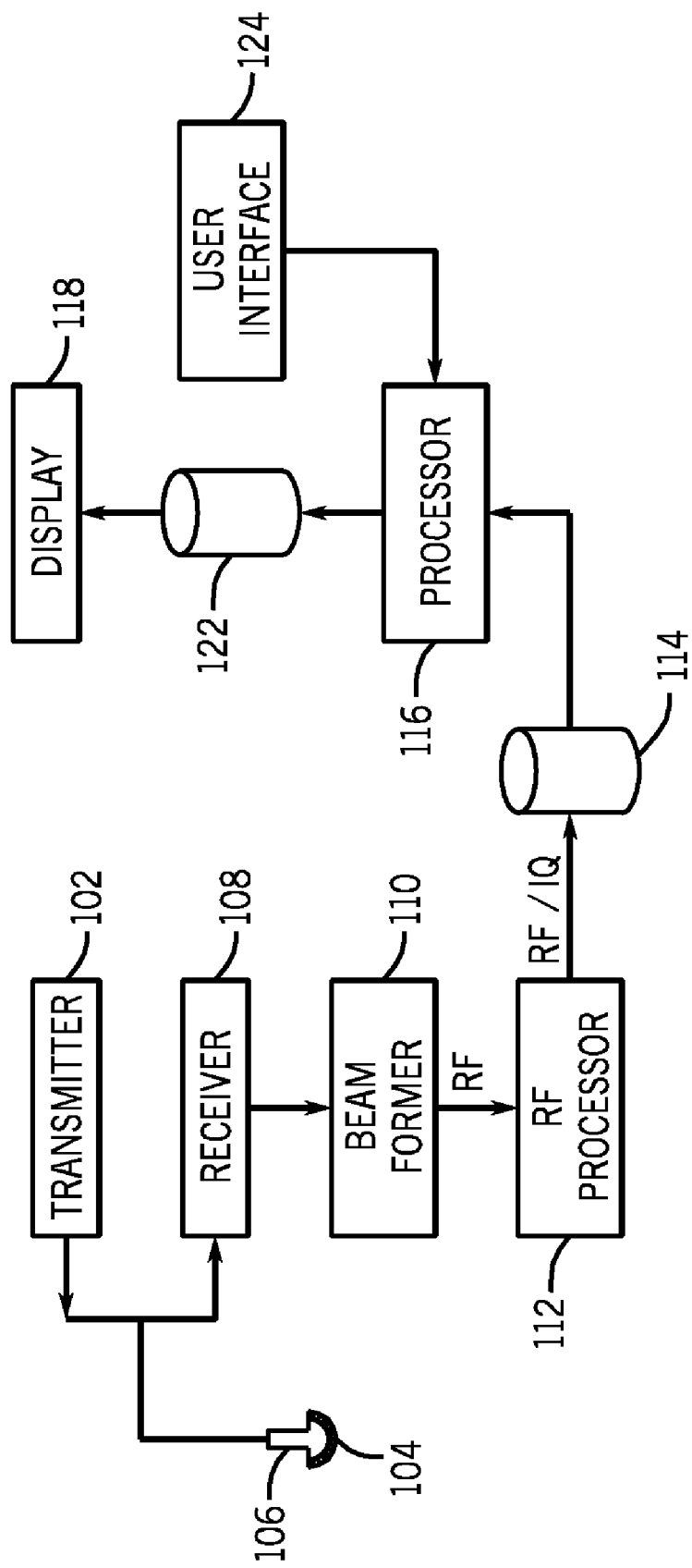
FIG. 1 is a block diagram of a diagnostic imaging system in which a connection arrangement in accordance with various embodiments of the invention is implemented.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Exemplary embodiments of diagnostic imaging systems are described in detail below. In particular, a detailed description of an exemplary diagnostic imaging system will first be provided followed by a detailed description of various embodiments of a connection arrangement for the diagnostic imaging system, especially for ultrasound imaging systems.

FIG. 1 is a block diagram of an ultrasound system 100 constructed in accordance with various embodiments of the invention. The ultrasound system 100 is capable of electrical or mechanical steering of a soundbeam (such as in 3D space) and is configurable to acquire information corresponding to a plurality of 2D representations or images of a region of interest (ROI) in a subject or patient. The ultrasound system 100 is configurable to acquire 2D images in one or more planes of orientation.

The ultrasound system 100 includes a transmitter 102 that, under the guidance of a beamformer 110, drives an array of elements 104 (e.g., piezoelectric elements) within a probe 106 to emit pulsed ultrasonic signals into a body. A variety of geometries may be used. The ultrasonic signals are backscattered from structures in the body, like blood cells or muscular tissue, to produce echoes that return to the elements 104. The echoes are received by a receiver 108. The received echoes are passed through the beamformer 110, which performs receive beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

In the above-described embodiment, the beamformer 110 operates as a transmit and receive beamformer. In an alternative embodiment, the probe 106 includes a 2D array with sub-aperture receive beamforming inside the probe. The beamformer 110 may delay, apodize and sum each electrical signal with other electrical signals received from the probe 106. The summed signals represent echoes from the ultrasound beams or lines. The summed signals a are output from the beamformer 110 to an RF processor 112. The RF processor 112 may generate different data types. e.g. B-mode, color Doppler (velocity/power/variance), tissue Doppler (velocity), and Doppler energy, for multiple scan planes or different scanning patterns. For example, the RF processor 112 may generate tissue Doppler data for three (tri-plane) scan planes. The RF processor 112 gathers the information (e.g. 1/Q, B-mode, color Doppler, tissue Doppler, and Doppler energy information) related to multiple data slices and stores the data information, which may include time stamp and orientation/rotation information, in the memory 114.

The ultrasound system 100 also includes a processor 116 to process the acquired ultrasound information (e.g., RF signal data or IQ data pairs) and prepare frames of ultrasound information for display on display 118. The processor 116 is adapted to perform one or more processing operations according to a plurality of selectable ultrasound modalities on the acquired ultrasound data. Acquired ultrasound data may be processed and displayed in real-time during a scanning session as the echo signals are received. Additionally or alternatively, the ultrasound data may be stored temporarily in memory 114 during a scanning session and then processed and displayed in an off-line operation.

The processor 116 is connected to a user interface 124 that may control operation of the processor 116 as explained below in more detail. A display 118 includes one or more monitors that present patient information, including diagnostic ultrasound images to the user for diagnosis and analysis. One or both of memory 114 and memory 122 may store two-dimensional (2D) or three-dimensional (3D) data sets of the ultrasound data, where such 2D and 3D data sets are accessed to present 2D (and/or 3D images). The images may be modified and the display settings of the display 118 also manually adjusted using the user interface 124.

It should be noted that although the various embodiments may be described in connection with an ultrasound system, the methods and systems, and in particular the connection arrangement described herein is not limited to ultrasound imaging or a particular configuration thereof. The various embodiments may be implemented in connection with different types of imaging systems, including, for example, x-ray imaging systems, magnetic resonance imaging (MRI) systems, computed-tomography (CT) imaging systems, positron emission tomography (PET) imaging systems, or combined imaging systems, among others. Further, the various embodiments may be implemented in non-medical imaging systems, for example, non-destructive testing systems such as ultrasound weld testing systems or airport baggage scanning systems.

Figure 2:
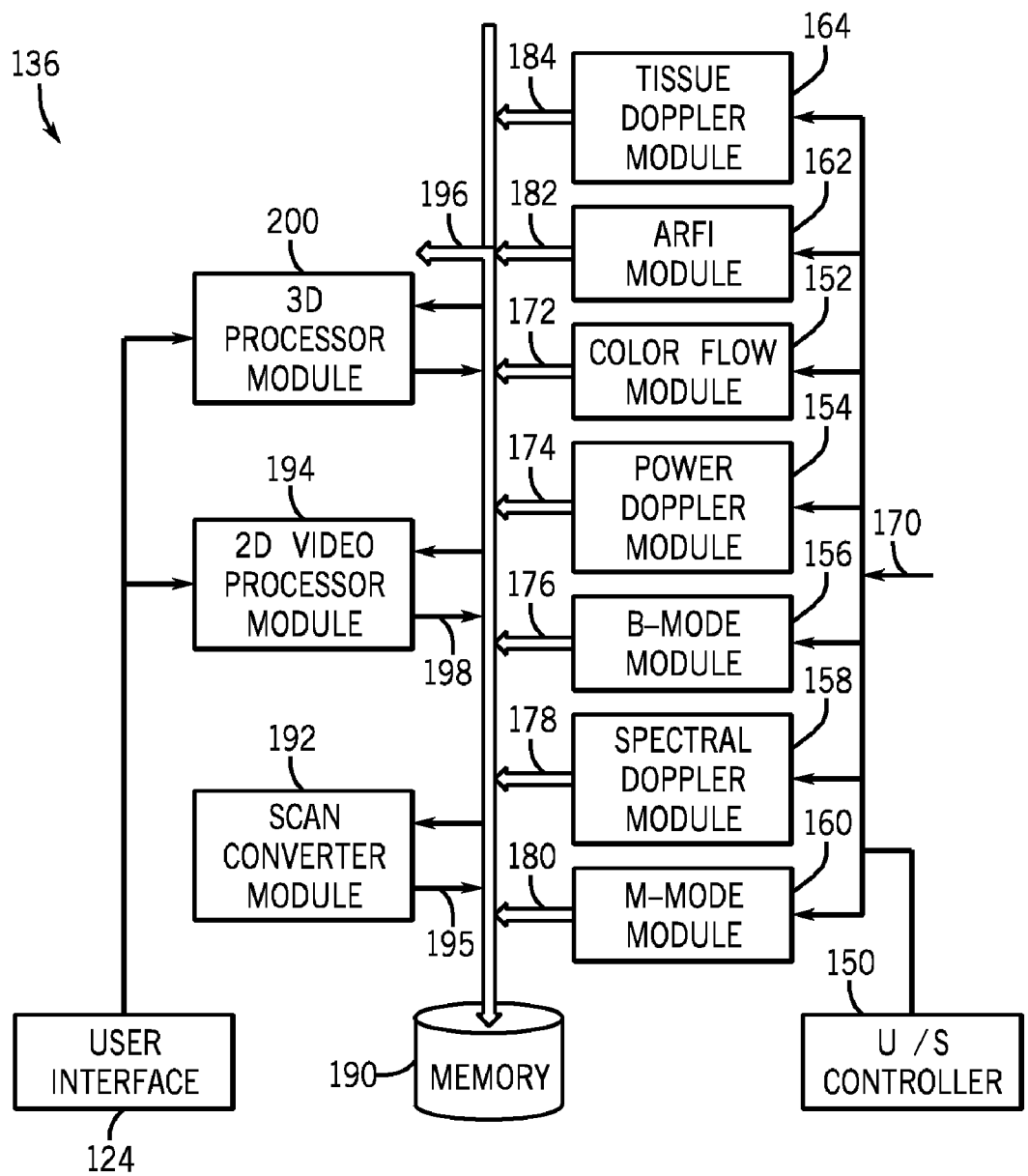
FIG. 2 is a block diagram of an ultrasound processor module of the diagnostic imaging system of FIG. 1 formed in accordance with various embodiments of the invention.

FIG. 2 illustrates an exemplary block diagram of an ultrasound processor module 136, which may be embodied as the processor 116 of FIG. 1 or a portion thereof. The ultrasound processor module 136 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 2 may be controlled by a local ultrasound controller 150 or by the processor module 136. The sub-modules 152-164 perform mid-processor operations. The ultrasound processor module 136 may receive ultrasound data 170 in one of several forms. In the embodiment of FIG. 2, the received ultrasound data 170 constitutes I,Q data pairs representing the real and imaginary components associated with each data sample. The I,Q data pairs are provided to one or more of a color-flow sub-module 152, a power Doppler sub-module 154, a B-mode sub-module 156, a spectral Doppler sub-module 158 and an M-mode sub-module 160. Optionally, other sub-modules may be included such as an Acoustic Radiation Force Impulse (ARFI) sub-module 162 and a Tissue Doppler (TDE) sub-module 164, among others.

Each of sub-modules 152-164 are configured to process the I,Q data pairs in a corresponding manner to generate color-flow data 172, power Doppler data 174, B-mode data 176, spectral Doppler data 178, M-mode data 180, ARFI data 182, and tissue Doppler data 184, all of which may be stored in a memory 190 (or memory 114 or memory 122 shown in FIG. 1) temporarily before subsequent processing. For example, the B-mode sub-module 156 may generate B-mode data 176 including a plurality of B-mode image planes, such as in a triplane image acquisition as described in more detail herein.

The data 172-184 may be stored, for example, as sets of vector data values, where each set defines an individual ultrasound image frame. The vector data values are generally organized based on the polar coordinate system.

A scan converter sub-module 192 accesses and obtains from the memory 190 the vector data values associated with an image frame and converts the set of vector data values to Cartesian coordinates to generate an ultrasound image frame 194 formatted for display. The ultrasound image frames 194 generated by the scan converter module 192 may be provided back to the memory 190 for subsequent processing or may be provided to the memory 114 or the memory 122.

Once the scan converter sub-module 192 generates the ultrasound image frames 194 associated with, for example, B-mode image data, and the like, the image frames may be restored in the memory 190 or communicated over a bus 196 to a database (not shown), the memory 114, the memory 122 and/or to other processors.

As an example, it may be desired to view functional ultrasound images or associated data (e.g., strain curves or traces) relating to echocardiographic functions on the display 118 (shown in FIG. 1). Strain information for display as part of the functional ultrasound images are calculated based on scan converted B-mode images. The scan converted data is then converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 118 (shown in FIG. 1), which may include one or more monitors or windows of the display, to display the image frame. The image displayed in the display 118 is produced from image frames of data in which each datum indicates the intensity or brightness of a respective pixel in the display.

Referring again to FIG. 2, a 2D video processor sub-module 194 combines one or more of the frames generated from the different types of ultrasound information. For example, the 2D video processor sub-module 194 may combine a different image frames by mapping one type of data to a grey map and mapping the other type of data to a color map for video display. In the final displayed image, color pixel data may be superimposed on the grey scale pixel data to form a single multi-mode image frame 198 (e.g., functional image) that is again re-stored in the memory 190 or communicated over the bus 196. Successive frames of images may be stored as a cine loop in the memory 190 or memory 122 (shown in FIG. 1). The cine loop represents a first in, first out circular image buffer to capture image data that is displayed to the user. The user may freeze the cine loop by entering a freeze command at the user interface 124. The user interface 124 may include, for example, a keyboard and mouse and all other input controls associated with inputting information into the ultrasound system 100 (shown in FIG. 1).

A 3D processor sub-module 200 is also controlled by the user interface 124 and accesses the memory 190 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

Figure 3:
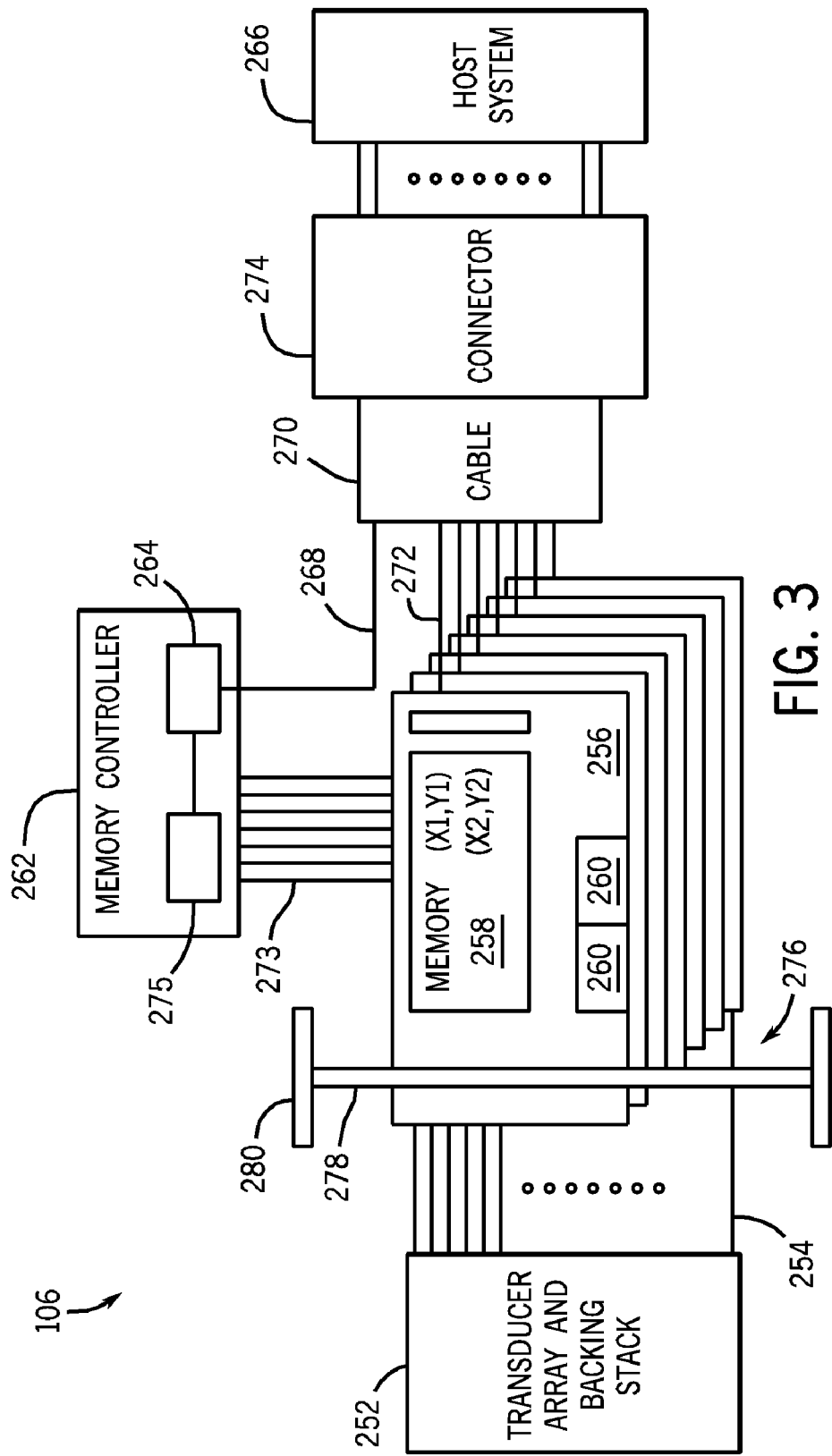
FIG. 3 is a block diagram of an ultrasound probe in communication with a host system having a connection arrangement formed in accordance with an exemplary embodiment of the present invention.

FIG. 3 illustrates a block diagram of an exemplary embodiment of the ultrasound probe 106 that may be used in connection with the ultrasound system 100 (both shown in FIG. 1). The ultrasound probe 106 includes a transducer array and backing stack 252 (the "transducer array 252"), transducer flexible (flex) cables 254, which may be formed as a scan head cable, and multiple processing boards 256 that support processing electronics. The transducer flex cables 254 and processing boards 256 may be arranged to form a connector stack or stacked connector as described in more detail herein. Each processing board 256 may includes a location memory 258 (which may include geometry RAM, encoder RAM, location registers and control registers as noted below) and signal processors 260. A location memory controller 262 (e.g., a general purpose CPU, microcontroller, PLD, or the like) also may be provided and includes a communication interface 264.

The communication interface 264 establishes data exchange with a host system 266 over communication lines 268 (e.g., digital signal lines) and through a system cable 270. Additionally, in an exemplary embodiment, the system cable 270 includes coaxial cables 272 that connect to the processing boards 256 to communicate transmit pulse waveforms to the transducer array 252 and communicate receive signals, after beamforming, to the host system 266. The probe 250 also may include a connector 274, through which the probe 250 connects to the host system 266.

A connection arrangement is provided that generally includes a clamping arrangement 276 to hold together and align the transducer flex cables 254 and the processing boards 256 in a stacked arrangement. The clamping arrangement 276 thereby aids in establishing electrical connectivity between the transducer flex cables 254 and the processing boards 256, as well as aligning connector ends of these components within the ultrasound probe 106. The clamping arrangement 276 may include a dowel pin 278 and a bolt 280, although other implementations are also suitable. Various embodiments of a connection arrangement that provide load distribution will be described in more detail below.

The transducer array 252 is bonded onto a backing stack. The transducer flex cables 254 provide electrical signal connections through the backing stack. In one exemplary embodiment, there is a plurality (e.g., forty-two) of transducer flex cables 254, each with a plurality (e.g., fifty) of signal connections. Thus, the transducer flex cables 254 support transmit and receive signal connections for many (e.g., 2100) transducer elements in the transducer array 252, although more or fewer may be used. For example, each processing board 256 may couple to six transducer flex cables 254, and thereby includes signal connections for 300 transducer elements.

The processing boards 256 may, like the flex cables 254, be formed from a flex material, such as, for example, polyimide, polyester, etc. The processing boards 256 include the processing electronics for the transducer array 252, including the signal processors 260 that perform beamforming on the receive apertures in the transducer array 252.

Each signal processor 260 may handle multiple, for example, four receive apertures defined at selected spatial locations on the transducer array 252. The receive apertures may be shaped (e.g., triangular) apertures that include a number of (e.g., fifteen) acoustic transducer elements arranged in rows, for example, as a row of five elements above a row of four elements above a row of three elements above a row of two elements above a row of one element. Furthermore, each processing board 256 may include a plurality (e.g., five) of signal processors 260. Thus, in the receive direction, each processing board 256 may process twenty receive apertures, each including fifteen acoustic transducer elements.

For every ultrasound beam, the location memory controller 262 connects via digital signal lines 273 (e.g., carried by a separate flex cable) to each location memory 258 on each processing board 256. The location memory controller 262 communicates the spatial location information into each location memory 258 for each receive aperture processed by the signal processors 260 on the processing boards 256. The digital signal lines 273 may include, for example, a clock line for each processing board 256, a serial command data line for each processing board 256, two data lines (for a total of fourteen data lines) connected to each processing board 256, an output enable for one or more of the signal processors 260, and a test signal.

The location memory controller 262 communicates with the host system 266 over the digital signal lines 273 that may form part of, for example, a synchronous serial port. To that end, the communication interface 264 and digital signal lines 273 may implement a low voltage differential signal interface, for example, including a coaxial cable with a grounded shield and center signal wire. The location memory controller 262 includes a block of cache memory 275, for example, 1-8 MBytes of static random access memory (SRAM).

Figure 4:
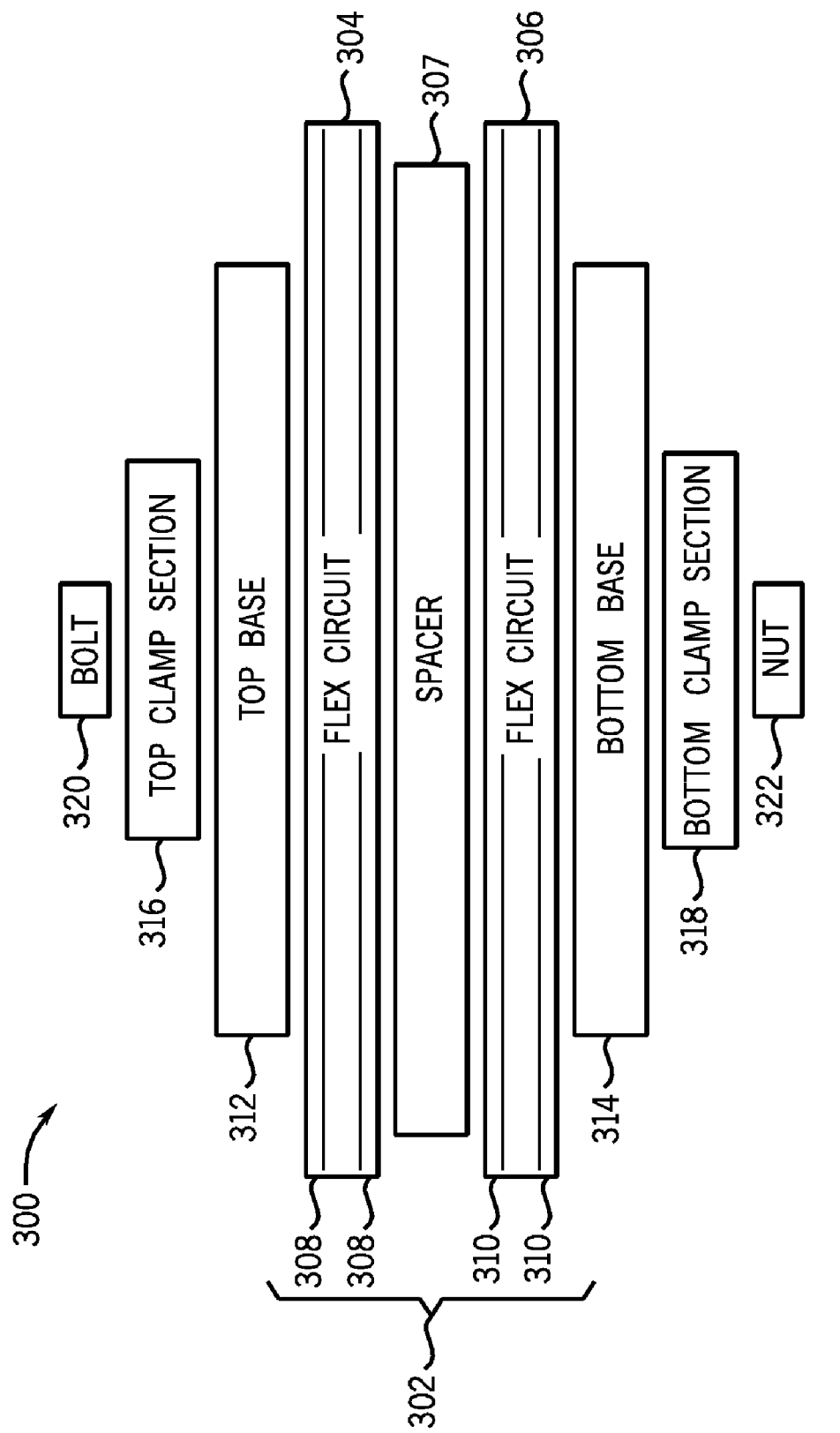
FIG. 4 is a simplified block diagram illustrating a connection arrangement for a stacked connector formed in accordance with various embodiments of the invention.

A connection arrangement for applying pressure to hold together and align, for example, the transducer flex cables 254 and the processing boards 256 in a stacked arrangement is configured in various embodiments to distribute or spread the pressure load across the stacked connector arrangement. For example, as shown in FIG. 4, a connection arrangement 300 is configured having a clamping configuration to apply pressure to a stacked connector 302, which is illustrated in this embodiment as a flex circuit 304 and a flex circuit 306 having a spacer 307 therebetween. Each of the flex circuits 304 and 306 include one or more circuit boards. For example, in some embodiments, the flex circuits 304 and 306 include a plurality of stacked circuit boards 308 and 310, respectively (four circuit boards are illustrated in the embodiment of FIG. 4). It should be noted additional flex circuits and spacers may be provided as desired or needed. For example, depending on the number of elements forming the array of transducer elements 104 of the ultrasound probe 106 (shown in FIG. 1), additional signal lines provided as part of the flex circuits may be needed to transmit and receive information between the array of transducer elements 104 and the host system 266 (shown in FIG. 3).

The stacked connector 302 is provided between a top base 312 and a bottom base 314, for example, sandwiched between the top base 312 and the bottom base 314. The top base 312 and the bottom base 314 hold together and maintain the connection of the stacked circuit boards 308 and 310 within each of the flex circuits 304 and 306, respectively. The top base 312 and the bottom base 314 also maintain the alignment of the components therebetween. It should be noted that the top base 312 and the bottom base 314 may be removed in some embodiments.

The connection arrangement 300 also includes a clamping arrangement, which comprises a top clamp section 316 adjacent the top base 312 and a bottom clamp section 318 adjacent to the bottom base 314 (or having the stacked connector 302 therebetween when the top base 312 and the bottom base 314 are removed). The clamping arrangement also includes a locking arrangement having, in the illustrated embodiment, a bolt 320 extending through the components of the connection arrangement 300, for example, from the top clamp section 316 to the bottom clamp section 318 and is secured with a nut 322. A washer 315 optionally may be provided between a head of the nut and the top base 312. Accordingly, tightening of the nut 322 compresses the top clamp section 316 and bottom clamp section 318 together, thereby compressing the components therebetween. For example, the compression from the tightening can press together contacts on each of the stacked circuit boards 308 and 310. Thus, a single bolt clamping arrangement is provided. The top base 312 and the bottom base 314 may be configured in some embodiments as spreader plates or load spreaders to facilitate spreading or distributing the compression force.

It should be noted that any locking arrangement may be provided that allows compression of the stacked connector 302, for example, between the top clamp section 316 and bottom clamp section 318. For example, a self clinching stud may be used that engages within an annulus.

The various components of the connection arrangement 300 may be formed from one or more materials. For example, the top clamp section 316 may be formed from a higher yield strength steel than the top base 312. In some embodiments, the top clamp section 316 is formed from spring steel and the top base 312 is formed from stainless steel. However, the top clamp section 316 may be formed from other materials, for example, magnesium, aluminum, glass or carbon reinforced plastic, etc. The bottom clamp section 318 and bottom base 314 may be similarly formed. Optionally, the bottom clamp section also may be formed from stainless steel, for example, when a self clinching stud is used for the locking arrangement. The spacers 307 may also be formed from different materials, for example, from aluminum. The flex circuits 304 and 306 may be formed from different circuit board materials, for example, a polyimide material with copper circuits printed thereon.

The connection arrangement 300 is configured to provide pressure across more than one contact point (e.g., more than one discrete contact point) from the applied force caused by the tightening of the bolt 320. In particular, the load from the compression force caused by the tightening of the bolt 320 is distributed or spread across the stacked connector 302. For example, the compression force is distributed by the top clamp section 316 and the bottom clamp section 318 to more than one point along the top base 312 and the bottom base 314, respectively. It should be noted that the compression force may be spread to any number of points along the top base 312 and the bottom base 314, for example, two points, three points, four points, etc. Moreover, the number of points may be increased (at the upper limit) such that force may be spread continuously over the top base 312 and the bottom base 314.

In some embodiments, for example, as illustrated in FIGS. 5 and 6, the top clamp section 316 and the bottom clamp section 318 are configured as pressure bars that extend outward from the bolt 320 a distance D on either side. The distance D that the top clamp section 316 and the bottom clamp section 318 extend may be the entire length of the top base 312 and bottom base 314, respectively, or any amount less than the entire length as described in more detail below.

The connection arrangement 300 shown in FIGS. 5 and 6 illustrates embodiments wherein the compression force is spread or distributed to two points along the top base 312 and bottom base 314. In particular, projections 340 extend from either the top base 312 and bottom base 314 or the top clamp section 316 and the bottom clamp section 318. The projections 340 may be spaced at the same or different distances from the bolt 320 and may be located at ends of the top clamp section 316 and the bottom clamp section 318 (as illustrated in FIGS. 5 and 6) or at a distance from the ends of the top clamp section 316 and the bottom clamp section 318. It should be noted that although only two projections 340 are shown on each side of the connection arrangement 300, additional projections 340 may be provided to distribute the compression force to more points along the top base 312 and the bottom base 314. It also should be noted that the projections 340 may be integrally formed with the top base 312 and bottom base 314 or the top clamp section 316 and the bottom clamp section 318 or separately formed and coupled to the top base 312 and bottom base 314 or the top clamp section 316 and the bottom clamp section 318.

The projections 340 may be provided in different shapes and sizes. Accordingly, although the projections 340 are illustrated as generally triangular elements, as described in more detail herein, the projections 340 may be cylindrical in shape, or any other shape as desired or needed (e.g., half-cylindrical, star shaped, etc.). The projections 340 are configured to provide a gap 342 between the top clamp section 316 and the bottom clamp section 318 and the top base 312 and bottom base 314, respectively.

It should be noted that the connection arrangement 300 illustrated in FIGS. 5 and 6 is shown as compressing not only flex circuits 304 and 306 and spacer 307, but additional flex circuits 330 and 332, as well as spacers 334 and 336.

As illustrated in FIG. 6, as the bolt 320 is tightened, the top clamp section 316 and the bottom clamp section 318 deflect towards the top base 312 and bottom base 314, respectively, within the gaps 342 such that pressure is applied to the top base 312 and bottom base 314 at each of the projections 340. In particular, arms 344 of the top clamp section 316 and the bottom clamp section 318 deflect towards, for example are elastically defaulted towards, the top base 312 and bottom base 314 as the bolt 320 is tightened.

Accordingly, the compression force is spread more evenly over the entire top base 312 and bottom base 314. Thus, connection of the various components is maintained across the entire length of the stacked connector 302 including at the corner regions (illustrated by the circles in FIG. 6).

The length of the arms 344 and the size or height of the projections 340 that form the gaps 342 may be varied. The positioning of the projections 340 also may be varied. For example, these elements may be varied based on the amount of pressure to be applied to the top base 312 and bottom base 314, temperature cycling conditions, etc. In some embodiments, the projections 340 are spaced about 10 millimeters from a center of the bolt 320 and both of the arms 344 are about 26 millimeters in combined length including the small distance the arms 344 extend past the projections 340. However, it should be noted that the distance between the projections 340 and the bolt 320 and the length of the arms 344 may be varied based on, for example, the amount of compression force to be applied. Other factors or variables that may be changed include, for example, circuitry and spacer stiffness, as well as overall clamp dimensions.

Variations to the connection arrangement 300 are contemplated. It should be noted that like numerals represent like parts in throughout the various embodiments. As shown in FIGS. 7 and 8, the top clamp section 316 and the bottom clamp section 318 are removed and resilient members 350 and 352 are positioned between the top base 312 and the flex circuit 304 and the bottom base 314 and the flex circuit 332. Additionally, instead of a nut 322, an opening 354 is formed within the bottom base 314 that receives therein an end of the bolt 320. The opening 354 may have grooves or other members to secure the bolt 320 therein or optionally the bolt 320 may be a self clinching stud that engages within the opening 354, which would include a nut replacing the head of the bolt 320.

The resilient members 350 and 352 may be sized, for example, have a thickness based on a compression force to be applied thereto as the bolt 320 is tightened. Additionally, the resilient members 350 and 352 may be formed from different materials. For example, the resilient members 350 and 352 may be formed from rubber, plastic, etc. The resilient members 350 and 352 may be formed from any material that allows the top base 312 and bottom base 314 to deflect when pressure is applied to the top base 312 and bottom base 314 by the head of the bolt 320.

Accordingly, the compression force is spread or distributed more evenly over the entire top base 312 and bottom base 314 as the resilient members 350 and 352 can deform to different degrees along the lengths of the resilient members 350 and 352. Thus, connection of the various components is maintained across the entire length of the stacked connector 302 including at the corner regions (illustrated by the circles in FIG. 7) where force moments tend to push upward at the ends of the components.

Figure 9:
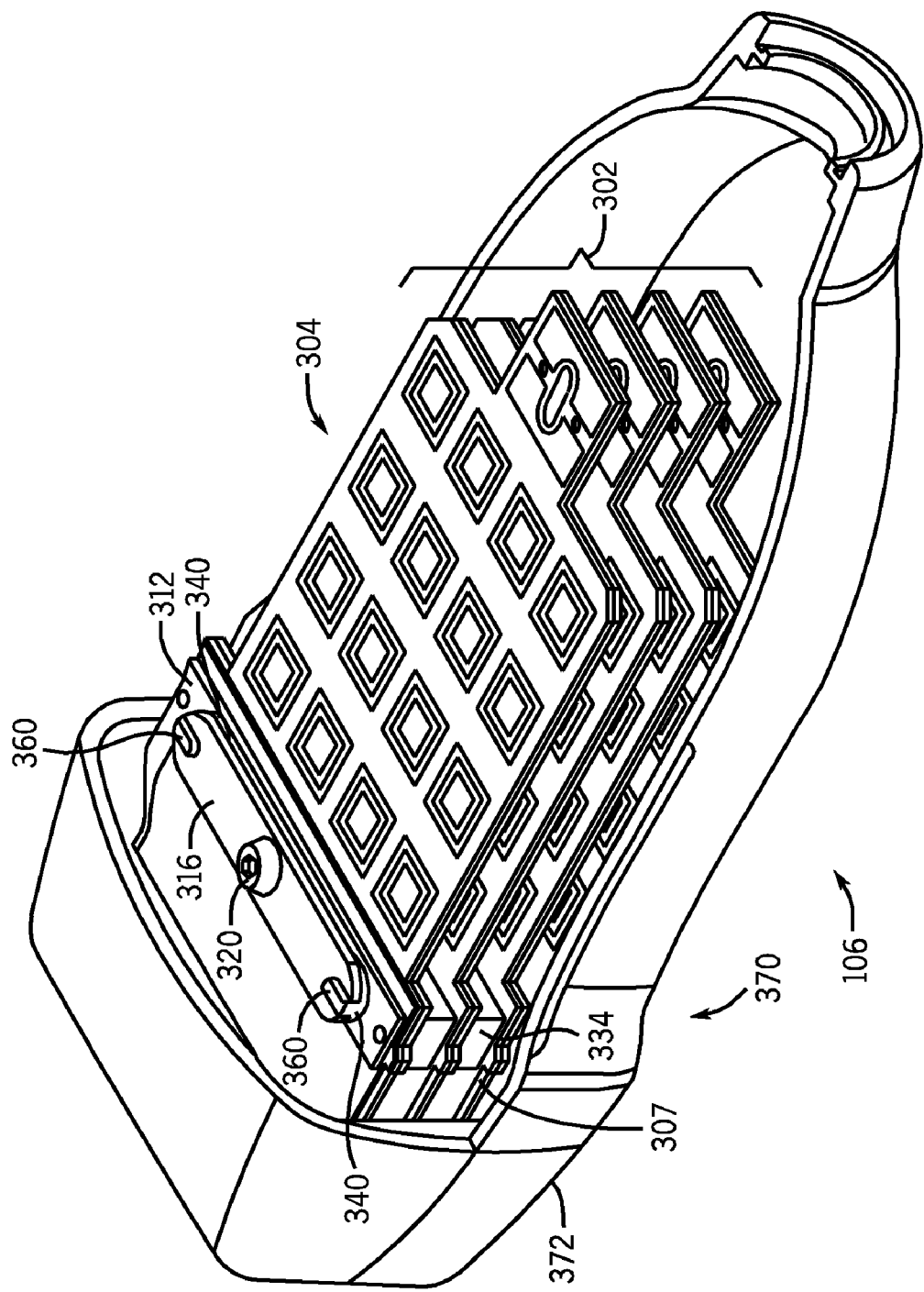
FIG. 9 is a top perspective view of a probe with part of the housing removed illustrating a connection arrangement for a stacked connector formed in accordance with an embodiment of the invention.
Figure 10:
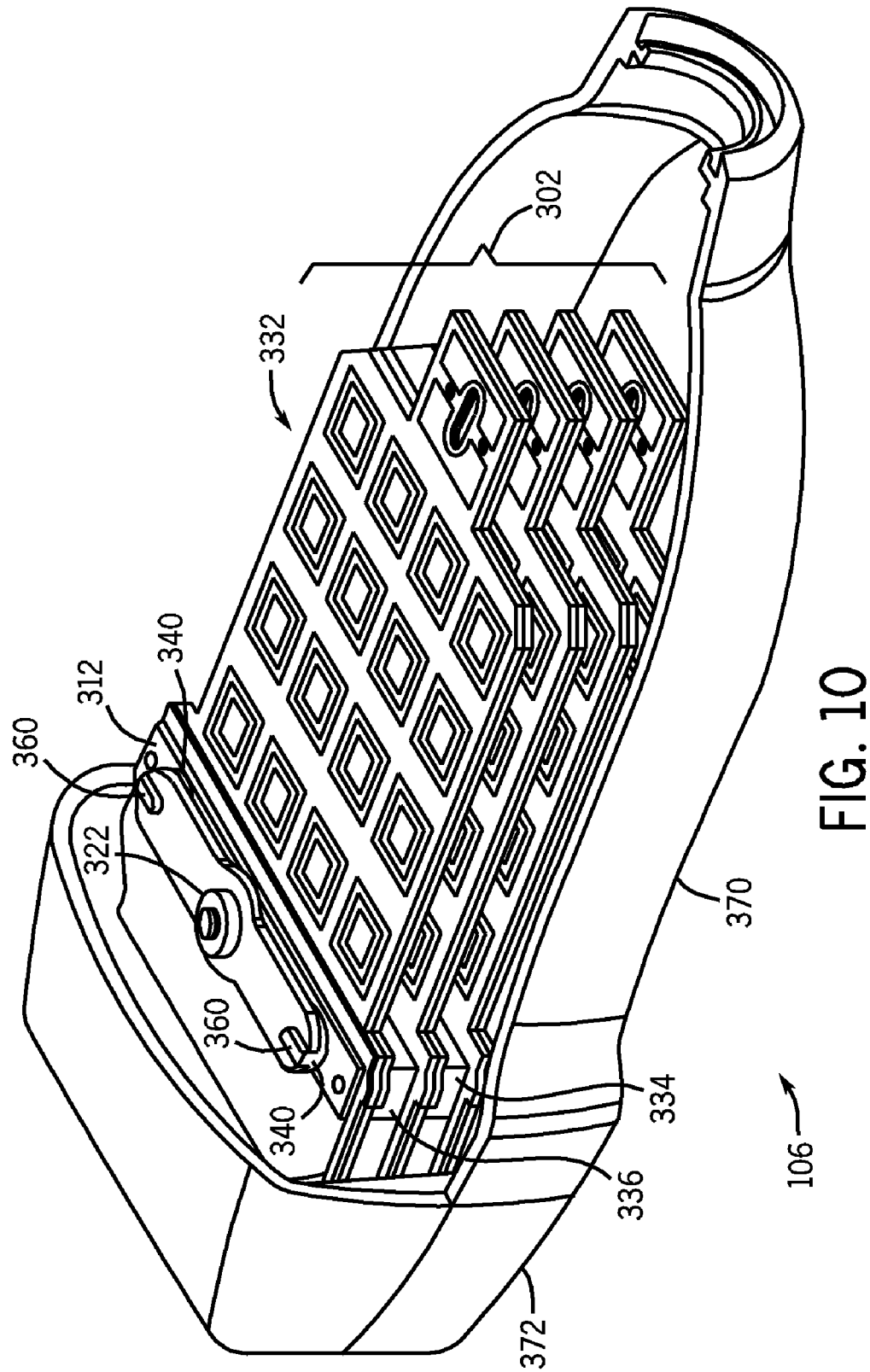
FIG. 10 is a bottom perspective view of a probe with part of the housing removed illustrating a connection arrangement for a stacked connector formed in accordance with an embodiment of the invention.

Additional components may be added to the connection arrangement 300 as shown in FIGS. 9 and 10 illustrating the ultrasound probe 106 formed in accordance with various embodiments. In particular, the projections 340 may be cylindrically shaped (pad shaped) or half-cylindrically shaped (e.g., half-moon or half-disc shaped) and extend from the top base 312 and the bottom base 314. In the half-cylindrically shaped embodiment, when the top clamp section 316 deflects, the contact between the top clamp section 316 and the half-cylindrically shaped projections 340 is a straight line. In this embodiment, the projections 340 are part of the top base 312 and the bottom base 314. Additionally, end stops 360 also may be provided, which may be formed as part of the projections 340 or separately therefrom. The end stops 360 are sized and shaped to receive therein the ends of the top clamp section 316 and the bottom clamp section 318. For example, the end stops 360 may be configured as tabs that engage both a portion of the ends of the top clamp section 316 and the bottom clamp section 318 and portions of the tops of the top clamp section 316 and the bottom clamp section 318. The end stops 360 are sized and shaped to maintain the position of the top clamp section 316 and the bottom clamp section 318 when the bolt 320 is rotated to apply the compression force. Accordingly, the end stops 360 resist or prevent rotation of the top clamp section 316 and the bottom clamp section 318 when the bolt 320 is rotated.

As can be seen in FIGS. 9 and 10, the connection arrangement 300 not only maintains the connection of the stacked connector 302, but also maintains the alignment of the stacked connector 302 within a housing 370 of the ultrasound probe 106 relative to connections at the transducer scanhead 372.

It should be noted that the top clamp section 316 and the bottom clamp section 318 may be shaped differently. For example, the top clamp section 316 may be configured as a pressure bar having generally straight elongated sides and the bottom clamp section 318 configured as a pressure bar having an outwardly curved middle section corresponding to where the bolt 320 is inserted through an opening (not visible) of the bottom clamp section 318.

Figure 11:
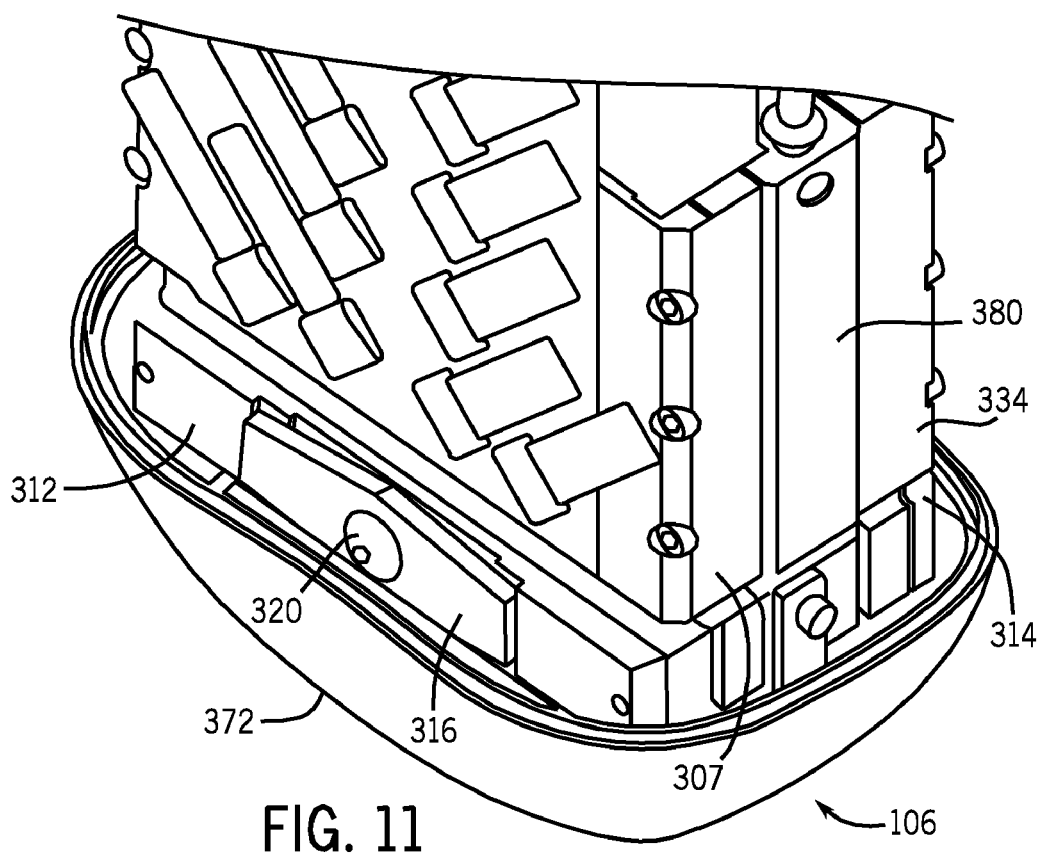
FIG. 11 is a perspective view of a probe with part of the housing removed illustrating a connection arrangement for a stacked connector formed in accordance with another embodiment of the invention.
Figure 12:
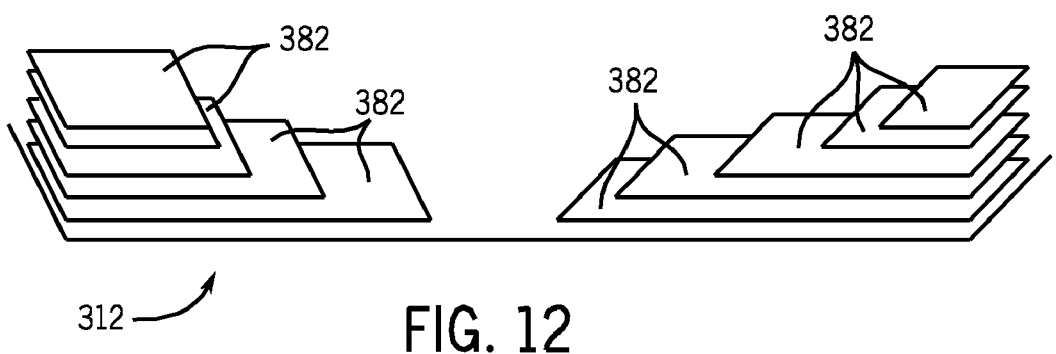
FIG. 12 is a perspective view of a top clamp section having a thickness formed in accordance with various embodiments of the invention.

Variations other modifications are contemplated for components other than the top clamp section 316 and the bottom clamp section 318. For example, as shown in FIG. 11, the top base 312 and bottom base 314 may have a varied thickness such that the thickness of the top the top base 312 and bottom base 314 increases, such as, in a stepwise configuration (as shown) or an angled configured to receive the top clamp section 316 and the bottom clamp section 318. It should be noted that in the illustrated embodiment, a single step configuration is effectively provided. Accordingly, the gap 342 between the top clamp section 316 and the bottom clamp section 318 and the top base 312 and bottom base 314, respectively, increases towards the bolt 320. Additionally, the top clamp section 316 in this embodiment has tapered sides increasing in width from a middle portion to each end. It should be noted that additional steps 382 may be provided, for example, as shown in FIG. 12. Additionally, and as described in more detail below, this step arrangement can be implemented in connection with a resilient member, for example, replacing the projection shown in FIG. 15.

Figure 13:
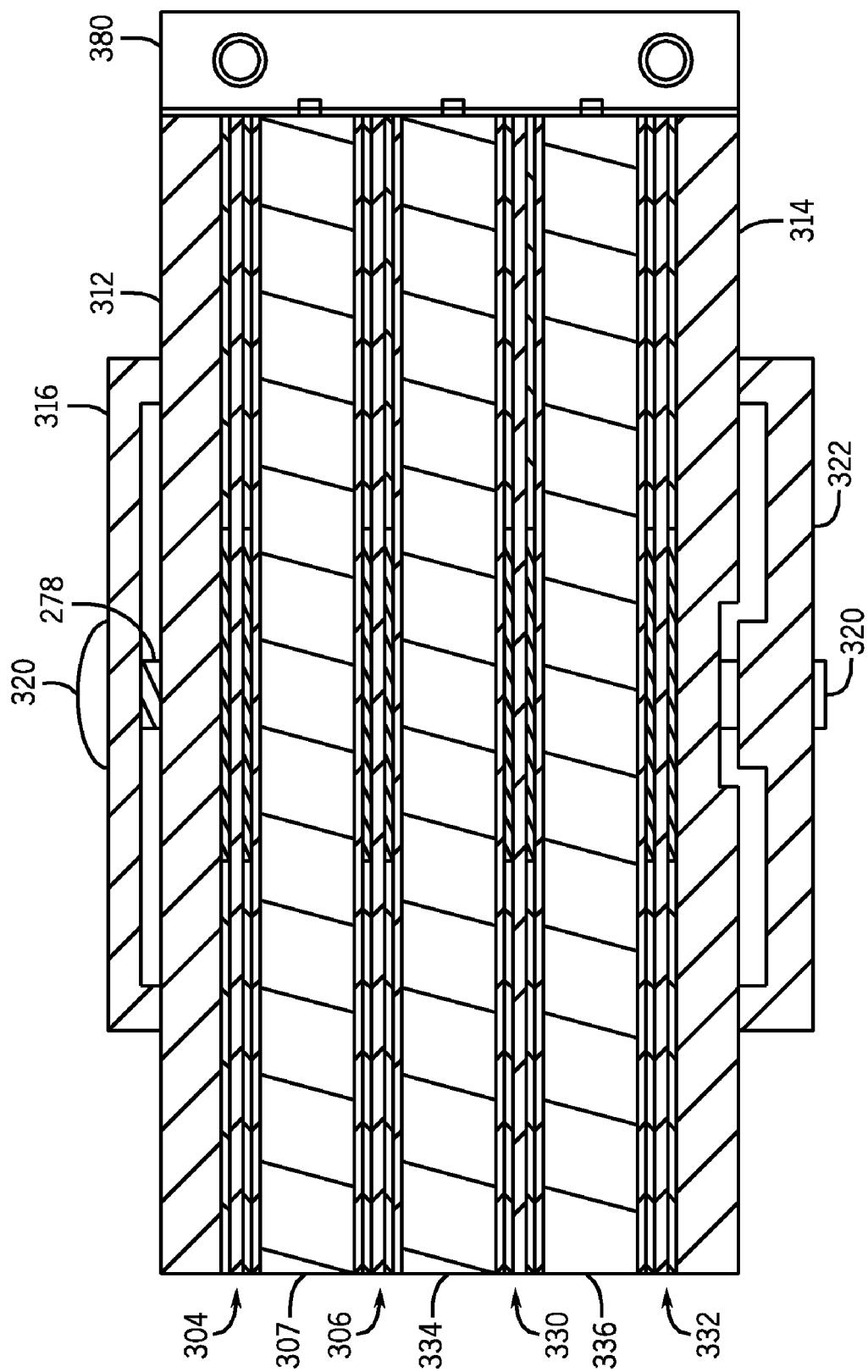
FIG. 13 is a cross-sectional view of a connection arrangement for a stacked connector formed in accordance with another embodiment of the invention.

Additional components may be provided as part of the ultrasound probe 106. For example, a heat exchanger 380 may be provided as shown in FIGS. 11 and 13. The heat exchanger 380 circulates cooling fluid within the ultrasound probe 106 as is known. Additionally, and for example, as shown in FIG. 14, each of the spacers may include alignment posts 390 for aligning each of the spacers in the stacked connector 302.

Accordingly, various embodiments of a connection arrangement distribute compression force over the entire surface of a stacked connector 302. Different elements may be used to distribute the compression force. For example, as shown in FIG. 15, angled projections 392 (e.g., rubber angled projections), namely having a tapered width, may be provided between the top clamp section 316 and top base 312. In the illustrated embodiment, the angled projection 392 is thicker away from the bolt 320. Similar angled projections 392 may be provided between the bottom clamp section 318 and bottom base 314. It should be noted that the angled projections 392 may be configured in a stepwise arrangement similar to that shown in FIG. 12.

Figure 17:
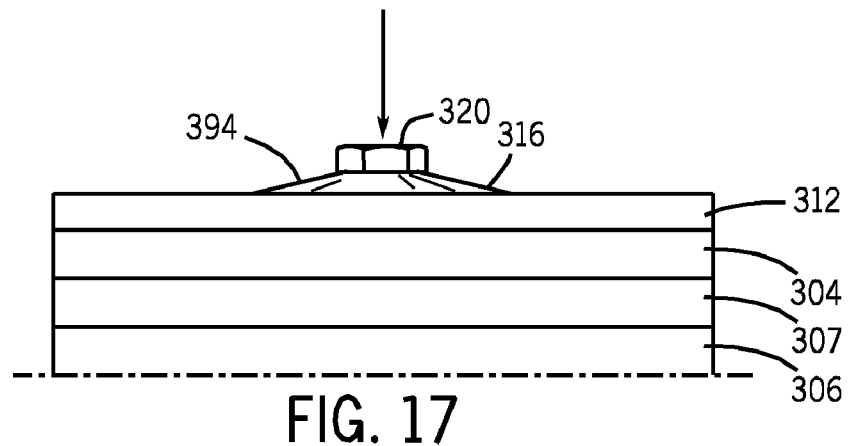
FIG. 17 is a cross-sectional view of a connection arrangement for a stacked connector formed in accordance with another embodiment of the invention.
Figure 18:
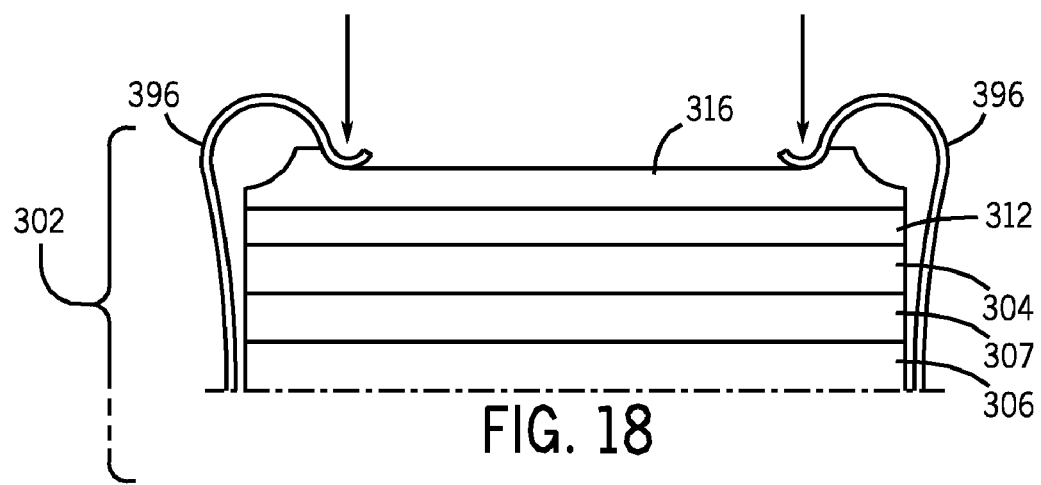
FIG. 18 is a cross-sectional view of a connection arrangement for a stacked connector formed in accordance with another embodiment of the invention.

In another embodiment as shown in FIG. 16, the top clamp section 316 may be formed as a pre-tensioned piece. For example, the top clamp section 316 may be curved upward toward the middle of the top clamp section 316. In still another embodiment as shown in FIG. 17, the top clamp section 316 may be a washer 394 that allows for thermal contraction and expansion. For example, the washer 394 may be a cupped spring washer (also referred to as a Belleville washer). In yet another embodiment as shown in FIG. 18, a spring clip 396 may be provided along each end of the stacked connector 302 to provide compression at each of the ends.

Figure 19:
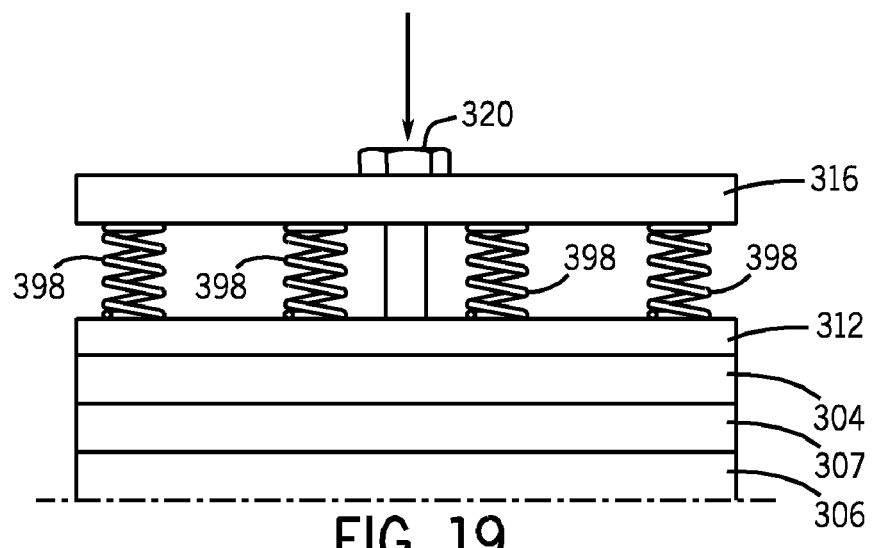
FIG. 19 is a cross-sectional view of a connection arrangement for a stacked connector formed in accordance with another embodiment of the invention.

In other embodiments, for example, as shown in FIG. 19, one or more springs 398 (or equivalent members, such as rubber elements or resilient members) may be provided between the top clamp section 316 and the top base 312. It should be noted that although four springs 398 are shown, more or less springs 398 may be provided and equally or unequally spaced. Additionally, some or all of the springs 398 may have equal or unequal stiffness.

Thus, various embodiments provide a connection arrangement for clamping stacked connectors such that the compression forced is more evenly distributed across the stacked connector. The various embodiments provide multiple points of contact at one or more distances from the applied force, such as the compression force from a bolt.

Figure 20:
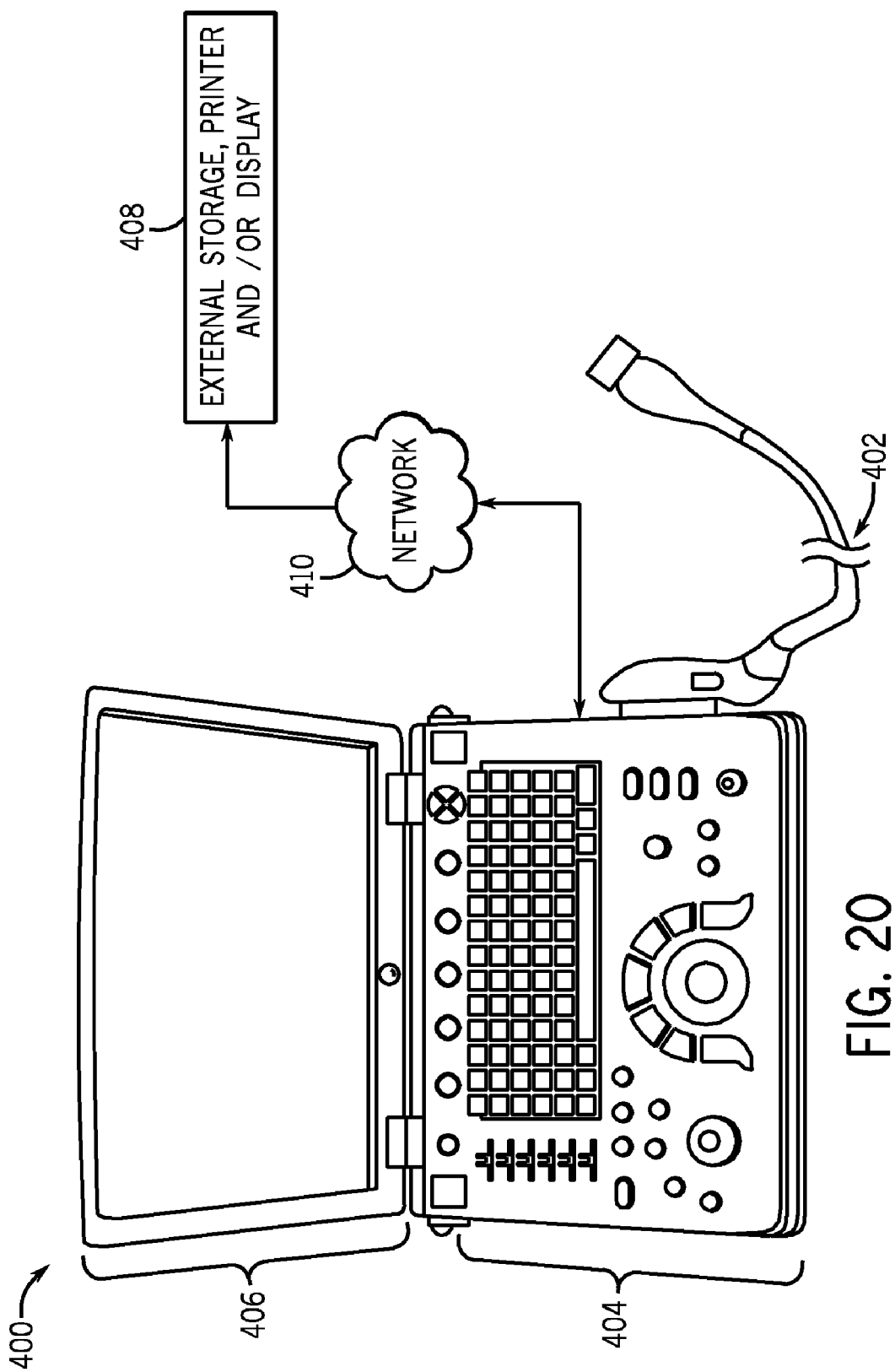
FIG. 20 illustrates a three-dimensional capable miniaturized ultrasound system formed in accordance with an embodiment of the invention.
Figure 21:
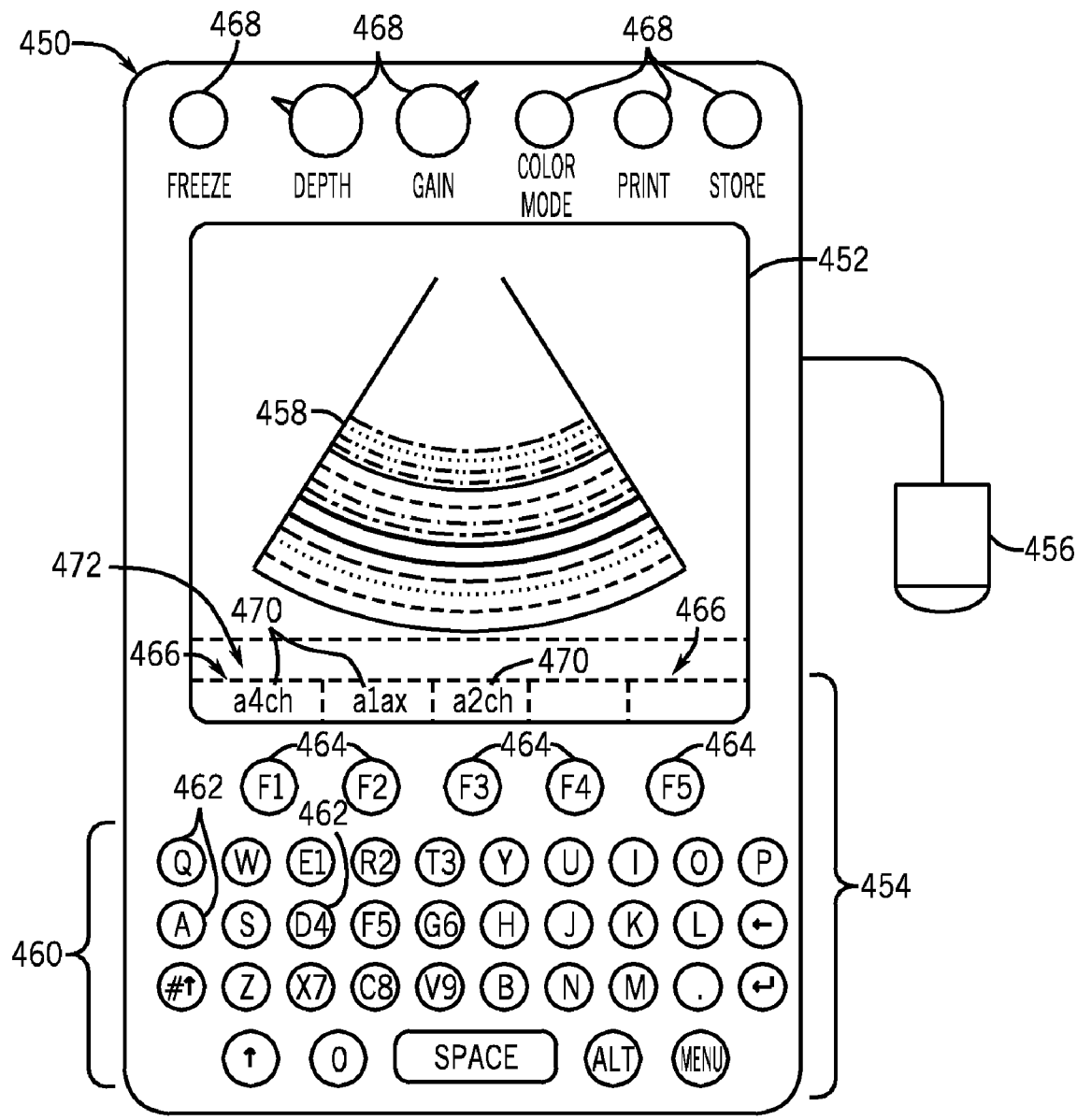
FIG. 21 illustrates a hand carried or pocket-sized ultrasound imaging system formed in accordance with an embodiment of the invention.
Figure 22:
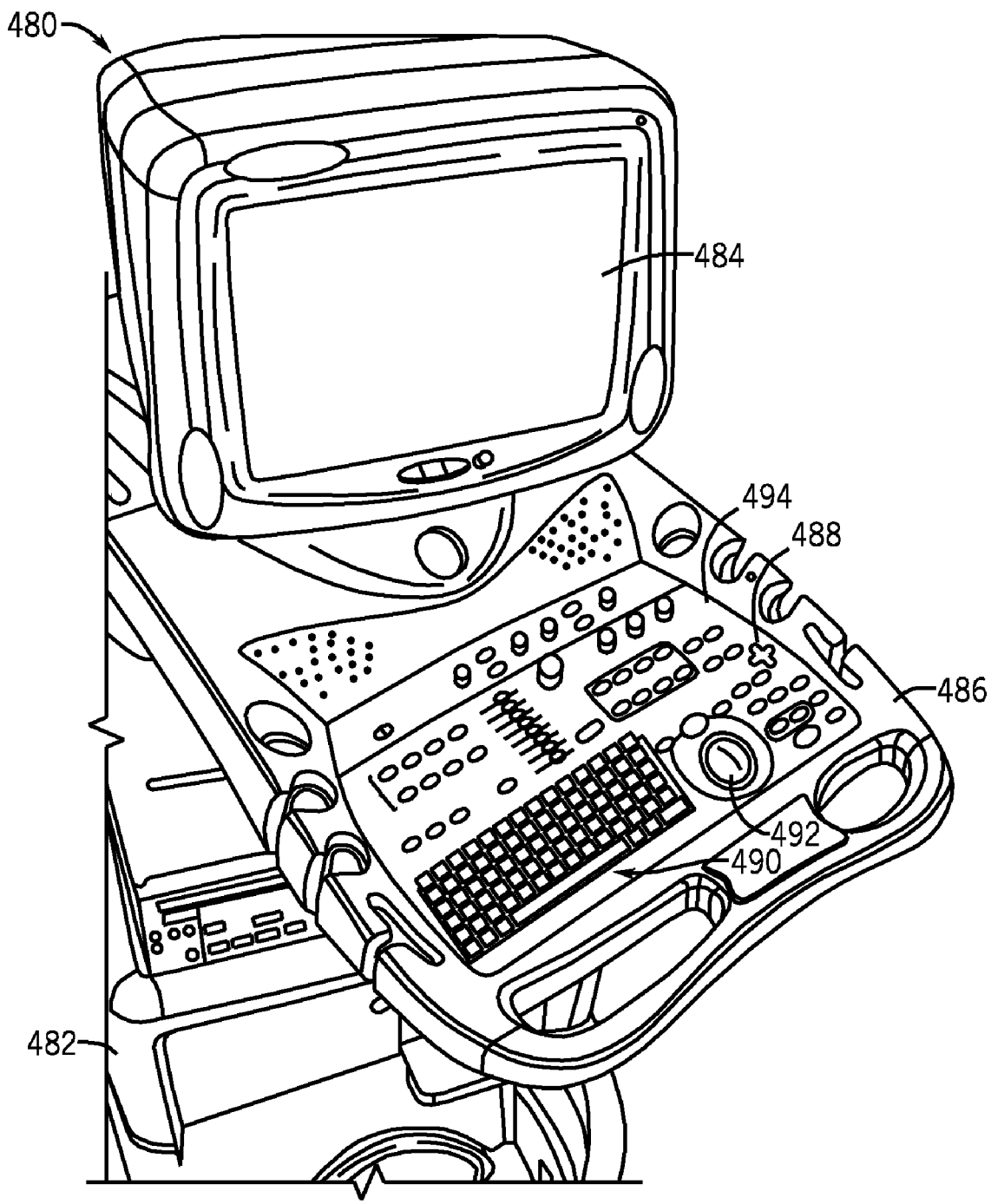
FIG. 22 illustrates a console type ultrasound imaging system formed in accordance with an embodiment of the present invention.

The ultrasound system 100 of FIG. 1 may be embodied in a small-sized system, such as laptop computer or pocket sized system as well as in a larger console-type system. FIGS. 20 and 21 illustrate small-sized systems, while FIG. 22 illustrates a larger system.

FIG. 20 illustrates a 3D-capable miniaturized ultrasound system 400 having a probe 402 that may be configured to acquire 3D or 3D ultrasonic data. For example, the probe 402 may have a 2D array of elements 104 as discussed previously with respect to the probe 106 of FIG. 1. A user interface 404 (that may also include an integrated display 406) is provided to receive commands from an operator. As used herein, "miniaturized" means that the ultrasound system 400 is a handheld or hand-carried device or is configured to be carried in a person's hand, pocket, briefcase-sized case, or backpack. For example, the ultrasound system 400 may be a hand-carried device having a size of a typical laptop computer. The ultrasound system 400 is easily portable by the operator. The integrated display 406 (e.g., an internal display) is configured to display, for example, one or more medical images.

The ultrasonic data may be sent to an external device 408 via a wired or wireless network 410 (or direct connection, for example, via a serial or parallel cable or USB port). In some embodiments, the external device 408 may be a computer or a workstation having a display. Alternatively, the external device 408 may be a separate external display or a printer capable of receiving image data from the hand carried ultrasound system 400 and of displaying or printing images that may have greater resolution than the integrated display 406.

FIG. 21 illustrates a hand carried or pocket-sized ultrasound imaging system 450 wherein the display 452 and user interface 454 form a single unit. By way of example, the pocket-sized ultrasound imaging system 450 may be a pocket-sized or hand-sized ultrasound system approximately 2 inches wide, approximately 4 inches in length, and approximately 0.5 inches in depth and weighs less than 3 ounces. The pocket-sized ultrasound imaging system 450 generally includes the display 452, user interface 454, which may or may not include a keyboard-type interface and an input/output (I/O) port for connection to a scanning device, for example, an ultrasound probe 456. The display 452 may be, for example, a 320×320 pixel color LCD display (on which a medical image 458 may be displayed). A typewriter-like keyboard 460 of buttons 462 may optionally be included in the user interface 454.

Multi-function controls 464 may each be assigned functions in accordance with the mode of system operation (e.g., displaying different views). Therefore, each of the multi-function controls 464 may be configured to provide a plurality of different actions. Label display areas 466 associated with the multi-function controls 464 may be included as necessary on the display 452. The system 450 may also have additional keys and/or controls 468 for special purpose functions, which may include, but are not limited to "freeze," "depth control," "gain control," "color-mode," "print," and "store."

One or more of the label display areas 466 may include labels 470 to indicate the view being displayed or allow a user to select a different view of the imaged object to display. For example, the labels 470 may indicate an apical 4-chamber view (a4ch), an apical long axis view (alax) or an apical 2-chamber view (a2ch). The selection of different views also may be provided through the associated multi-function control 464. For example, the 4ch view may be selected using the multi-function control F5. The display 452 may also have a textual display area 472 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 450 and the miniaturized ultrasound system 400 of FIG. 20 may provide the same scanning and processing functionality as the system 100 (shown in FIG. 1).

FIG. 22 illustrates a portable ultrasound imaging system 480 provided on a movable base 482. The portable ultrasound imaging system 480 may also be referred to as a cart-based system. A display 484 and user interface 486 are provided and it should be understood that the display 484 may be separate or separable from the user interface 486. The user interface 486 may optionally be a touchscreen, allowing the operator to select options by touching displayed graphics, icons, and the like.

The user interface 486 also includes control buttons 488 that may be used to control the portable ultrasound imaging system 480 as desired or needed, and/or as typically provided. The user interface 486 provides multiple interface options that the user may physically manipulate to interact with ultrasound data and other data that may be displayed, as well as to input information and set and change scanning parameters and viewing angles, etc. For example, a keyboard 490, trackball 492 and/or multi-function controls 494 may be provided.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising", and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A connection arrangement for a stacked connector in a diagnostic imaging system, the connection arrangement comprising:
    a top clamp section;
    a bottom clamp section;
    a stacked connector between the top clamp section and the bottom clamp section; and
    a plurality of projections forming a gap between at least one of (i) the top clamp section and the stacked connector or (ii) the bottom clamp section and the stacked connector, at least one of the top clamp section or the bottom clamp section comprising arms, the projections extending between the arms and the stacked connector, wherein the top clamp section and the bottom clamp section are configured to distribute a compression force along a plurality of points of the stacked connector, the arms comprising a material configured to deflect under the compression force.

2. A connection arrangement in accordance with claim 1 wherein the stacked connector comprises a plurality of flexible circuits having a plurality of spacers therebetween.

3. A connection arrangement in accordance with claim 1 further comprising a top base between the top clamp section and the stacked connector and a bottom base between the bottom clamp section and the stacked connector.

4. A connection arrangement in accordance with claim 1 wherein the projections extend from the top clamp section and the bottom clamp section.

5. A connection arrangement in accordance with claim 1 further comprising a top base between the top clamp section and the stacked connector and a bottom base between the bottom clamp section and the stacked connector and wherein the projections extend from at least one of the top base or the bottom base.

6. A connection arrangement in accordance with claim 1 further comprising a resilient member between at least one of (i) the top clamp section and the stacked connector and (ii) the bottom clamp section and the stacked connector.

7. A connection arrangement in accordance with claim 1 further comprising end stops to maintain a position of the top clamp section and the bottom clamp section.

8. A connection, arrangement in accordance with claim 7 wherein the end stops are configured to resist rotation of the top clamp section and the bottom clamp section.

9. A connection arrangement in accordance with claim 1 further comprising a top base between the top clamp section and the stacked connector and a bottom base between the bottom clamp section and the stacked connector, and wherein at least one of the top base and bottom base comprise a varying stepwise width.

10. A connection arrangement in accordance with claim 1 further comprising a resilient member between at least one of (i) the top clamp section and the stacked connector and (ii) the bottom clamp section and the stacked connector, the resilient member having one of a constant width and a tapered width.

11. A connection arrangement in accordance with claim 1 wherein at least one of the top clamp section and the bottom clamp section comprises a pre-tensioned piece 12. A connection arrangement in accordance with claim 1 further comprising a top base between the top clamp section and the stacked connector and a cupped spring washer and a bolt extending from the top clamp section to the bottom clamp section, wherein the bolt comprises a head, and wherein the cupped spring washer is positioned between the head and the top base.

13. A connection arrangement in accordance with claim 1 further comprising a spring clip along each end of the stacked connector to provide compression at each of the ends.

14. A connection arrangement in accordance with claim 1 further comprising a plurality of springs between at least one of (i) the top clamp section and the stacked connector and (ii) the bottom clamp section and the stacked connector.

15. A connection arrangement in accordance with claim 1 further comprising a top base between the top clamp section and the stacked connector and a bottom base between the bottom clamp section and the stacked connector and wherein the top clamp section is formed from a higher yield strength steel than the top base.

16. A connection arrangement in accordance with claim 1, wherein the stacked connector extends a height along a central axis, the projections comprising radially inner segments and radially outer segments, the radially inner segment of each projection extending closer to the central axis than the radially outer segment of the corresponding projection, the radially outer segment of each projection extending outwardly from the radially inner segment of the corresponding projection in a direction away from the central axis, wherein the projections comprise at least one of angled ramps or steps such that at least a portion of the radially outer segment of each projection has a thickness defined along the central axis that is greater than a thickness of the radially inner segment of the corresponding projection.

17. A connector for an ultrasound probe, the connector comprising:
    a plurality of transducer flexible cables;
    a plurality of processing boards, the plurality of flexible cables and the plurality of processing boards forming a stacked connector; and
    a clamping arrangement configured to apply pressure to the stacked connector to electrically connect the plurality of transducer flexible cables and the plurality of processing boards, the clamping arrangement comprising:
        a top clamp section;
        a bottom clamped section, wherein the stacked connector is between the top clamp section and the bottom clamp section;
        a top base between the to clamp section and the stacked connector; and
        a bottom base between the bottom clamp section and the stacked connector, at least one of the top base and bottom base having a varied thickness, wherein the clamping arrangement is configured to distribute a compression force from the applied pressure along a plurality of points of the stacked connector.

18. A connector in accordance with claim 17, wherein at least one of the top base or the bottom base has one of a stepwise configuration or an angled configuration.

19. A method for interconnecting components within a diagnostic imagine system, the method comprising:
    aligning a plurality of flexible circuits to form a stacked connector;
    positioning the stacked connector between a top clamp section and a bottom clamp section; and
    distributing a compression force along a plurality of points of the stacked connector by moving the top and bottom clamping members toward each other, wherein at least one of the top clamping member or the bottom clamping member deflects during the movement.

* * * * *

UNITED STATES PATENT AND TRADEMARK OFFICE
CERTIFICATE OF CORRECTION

| | |
|---|---|
| PATENT NO. | : 8,062,040 B2 |
| APPLICATION NO. | : 12/433474 |
| DATED | : November 22, 2011 |
| INVENTOR(S) | : Konkle et al. |

It is certified that error appears in the above-identified patent and that said Letters Patent is hereby corrected as shown below:

In Column 4, Line 11, delete "a are" and insert -- are --, therefor.

In Column 4, Line 13, delete "types." and insert -- types, --, therefor.

In Column 4, Line 18, delete "1/Q," and insert -- I/Q, --, therefor.

In Column 9, Line 63, delete "defaulted" and insert -- deformed --, therefor.

In Column 15, Line 48, in Claim 8, delete "connection," and insert -- connection --, therefor.

In Column 16, Line 44, in Claim 17, delete "to" and insert -- top --, therefor.

In Column 16, Line 55, in Claim 19, delete "imagine" and insert -- imaging --, therefor.

Signed and Sealed this
Twenty-seventh Day of March, 2012

David J. Kappos
*Director of the United States Patent and Trademark Office*